(12) United States Patent
Martin

(10) Patent No.: US 8,061,633 B2
(45) Date of Patent: Nov. 22, 2011

(54) APPARATUS FOR USE IN SAMPLE ANALYSIS

(75) Inventor: John Martin, Annandale, NJ (US)

(73) Assignee: SPEX Sample Prep LLC, Metuchen, NJ (US)

( * ) Notice: Subject to any disclaimer, the term of this patent is extended or adjusted under 35 U.S.C. 154(b) by 605 days.

(21) Appl. No.: 12/169,757

(22) Filed: Jul. 9, 2008

(65) Prior Publication Data

US 2010/0006681 A1    Jan. 14, 2010

(51) Int. Cl.
*B02C 11/08* (2006.01)
(52) U.S. Cl. ......................................................... 241/23
(58) Field of Classification Search ........... 241/DIG. 37, 241/23, 65, 175, 179; 435/6, 91.1
See application file for complete search history.

(56) References Cited

U.S. PATENT DOCUMENTS

| | | | | |
|---|---|---|---|---|
| 3,534,914 A | * | 10/1970 | Chaplenko | 241/66 |
| 3,762,659 A | * | 10/1973 | Aegidius | 241/199 |
| 4,307,846 A | * | 12/1981 | Spelsberg | 241/246 |
| 4,509,695 A | * | 4/1985 | Bessman | 241/2 |
| 5,829,696 A | * | 11/1998 | DeStefano et al. | 241/169 |
| 6,695,236 B2 | * | 2/2004 | Gazeau | 241/2 |
| 7,370,819 B2 | * | 5/2008 | Czarnek | 241/2 |
| 2004/0053319 A1 | | 3/2004 | McWilliams et al. | |
| 2004/0115720 A1 | | 6/2004 | McWilliams et al. | |

OTHER PUBLICATIONS

International Search Report of International Application No. PCT/US2009/49022, Filed: Jun. 29, 2009.
International Preliminary Report on Patentability, dated Jan. 20, 2011 of International Application No. PCT/US2009/49022, filed Jun. 29, 2009.

* cited by examiner

*Primary Examiner* — David J. Walczak
*Assistant Examiner* — Jennifer C Chiang
(74) *Attorney, Agent, or Firm* — Sorin Royer Cooper LLC

(57) ABSTRACT

A vial and impactor combination for use in a cryogenic mill is disclosed. The impactor includes a steel or similar core, and a surrounding exterior of polycarbonate or similar inert material. The vial is made preferably of polycarbonate with endcaps also made of polycarbonate.

5 Claims, 3 Drawing Sheets

Schematic drawing of Freezer/Mill grinding action.

Schematic drawing of Freezer/Mill grinding action.

APPARATUS FOR USE IN SAMPLE ANALYSIS

TECHNICAL FIELD

This invention relates to sample analysis, and more specifically, to a method and apparatus for us in cryogenic laboratory mills that chill samples to liquid nitrogen temperatures and pulverize the chilled sample with an impactor. The invention has particular applicability in systems that create powder from otherwise hard to grind samples, such as biological soft tissue.

BACKGROUND OF THE INVENTION

Cryogenic mills are well known in the art and are used in a variety of scientific applications. Such applications include toxicity testing, DNA analysis, etc.

Such cryogenic mills typically operate by placing a sample in a vial, and then submerging the vial in a cooling fluid such as liquid nitrogen. The sample is then made extremely cold, so that it is amenable to be pulverized. The cold also prevents heat buildup which could cause degradation of samples such as RNA in biological tissue. Also included within the vial is a steel impactor for providing an impactor force.

In operation, the impactor is oscillated while kept cool and the impactor repeatedly impacts upon the sample in the vial. This repeated impacting grinds the sample into a powder by essentially pulverizing it. The powder can then be used in a variety of scientific analyses, such as DNA testing, etc.

One problem with the arrangement is that the impactor itself is typically stainless steel. In some applications, data gathered from analyzing the pulverized sample can be corrupted due to the fact that the steel impactor contaminates the composition of the pulverized sample itself. However, as the impactor must be driven most efficiently by an alternating electromagnetic field, and material that is hard enough to grind a very cold sample must be used, it is difficult to overcome both of the above.

Moreover, as the steel impactor is quite hard, the end pieces of the substantially cylindrical vial that are typically impacted by the impactor are also made of steel, as anything softer would likely be destroyed by the impactor.

In view of the above, there exists a need in the art for a vial and associated apparatus for use in a cryogenic mill which overcomes the foregoing issues.

SUMMARY OF THE INVENTION

The above and other problems of the prior art are overcome in accordance with the present invention which relates to a novel impactor and vial combination to facilitate low temperature grinding of samples in a cryogenic mill.

In accordance with one embodiment of the invention, a grinder is utilized which is manufactured from a steel dowel surrounded by two members, each of which has been hollowed to include a trough. The steel impactor core is inserted into the troughs so that the members surround the impactor core, and the ends of the members are joined together, thereby creating an impactor core sealed within the members. The members are preferably of polycarbonate.

Preferably, a vial to be inserted into the liquid nitrogen or other cooling fluid is made of polycarbonate, which can withstand the force of the impactor even at low temperatures. The polycarbonate coated steel impactor core, coupled with the polycarbonate vial, provides sufficient impact between the two to grind the sample. The vial may be made of a relatively thin cylindrical wall of polycarbonate, and two end caps of solid polycarbonate, which end caps are thick enough to withstand the repeated impacting of the polycarbonate coated impactor core.

DETAILED DESCRIPTION OF THE PREFERRED EMBODIMENTS

Figure 1:
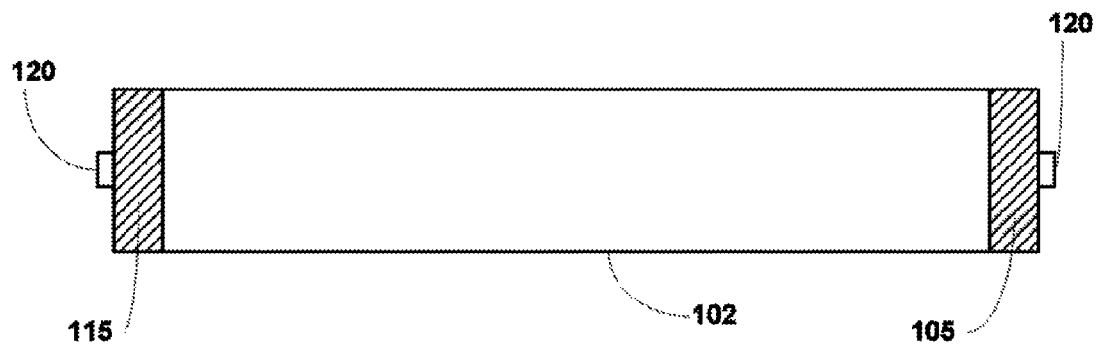
FIG. 1 depicts an exemplary vial.

FIG. 1 depicts an exemplary vial 101 that may be utilized in connection with the present invention. The vial includes a main body portion 102 and cap portions 105 and 115. The cap portions are preferably frictionally fitted into the main body portion 102, and may be supported in the cryogenic mill by supports that push the caps 105 and 115 towards each other. The caps themselves may have attachments on the tops thereof, such as a threaded opening or protruding threaded member, clip, or other structure to allow removal of the caps by a special extraction tool or manually.

In one embodiment, the main portion 102 is entirely manufactured from polycarbonate. Both the main body and the cap portions must be capable of withstanding the temperatures induced by being submerged in liquid nitrogen. However, the cap portions 105 and 115 must also be of sufficient thickness to withstand the alternating and repeated impacting.

Figure 2:
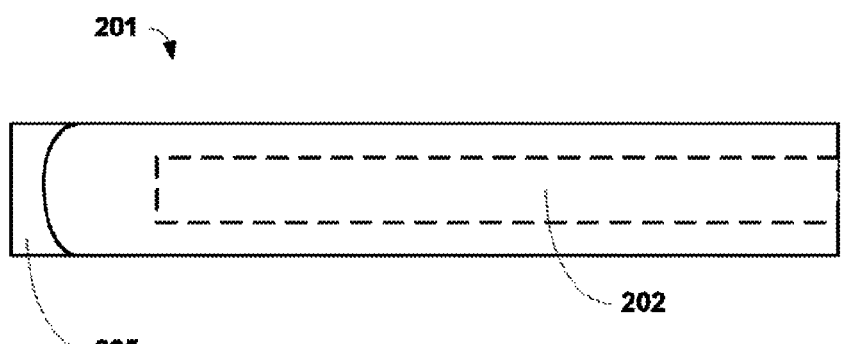
FIG. 2 depicts a cross section of one of the members that can be used to surround the steel impactor, and also depicts the hollowing of such member to form a trough.
Figure 3:
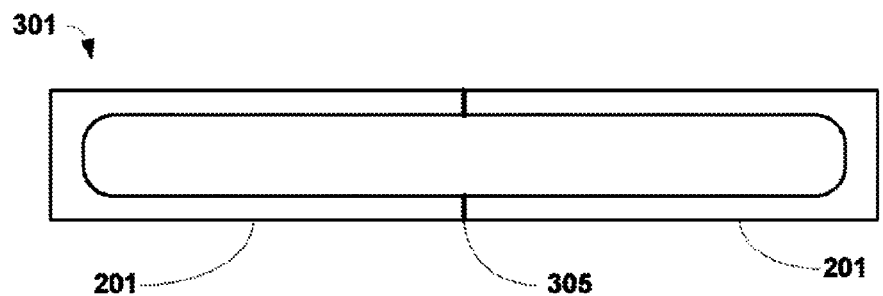
FIG. 3 is a depiction of the assembled impactor, including the surrounding members and a steel impactor core.

FIG. 2 depicts a member 201 preferably also made of polycarbonate. The member of FIG. 2 is intended to be utilized as part of a process for manufacturing the impactor that will be used within the vial 101. The dotted outline in FIG. 2 shows a polycarbonate tube surrounding the steel impactor with end plugs. There is a thickened portion 205 of polycarbonate on the end of the impactor core as shown. The remaining portions of the polycarbonate coating may be formed by boring a trough into a solid cylindrical polycarbonate member.

It has been found empirically that the distance 205 can optimally be set to 5 mm, although the thickness of the polycarbonate coating around the remainder of the impactor core is approximately 2 mm. Other thicknesses and dimensions are possible as well.

To assemble the impactor, two members of the type shown as 201 are constructed by drilling longitudinally nearly all the way through solid cylindrical members. Alternatively, if the member is made from a moldable material, the material can simply be molded into the shape showing in FIG. 2, including the trough running nearly all the way through the center.

A steel impactor core 302 is fitted into the trough created in each of two members. The center of the members are then joined at 305 by welding and/or glue or other means. The completed impactor is now ready to be utilized in a cryogenic mill. The impactor core is of course responsive to a magnetic force, which can be used to oscillate the impactor in a manner known in the art.

Figure 4:
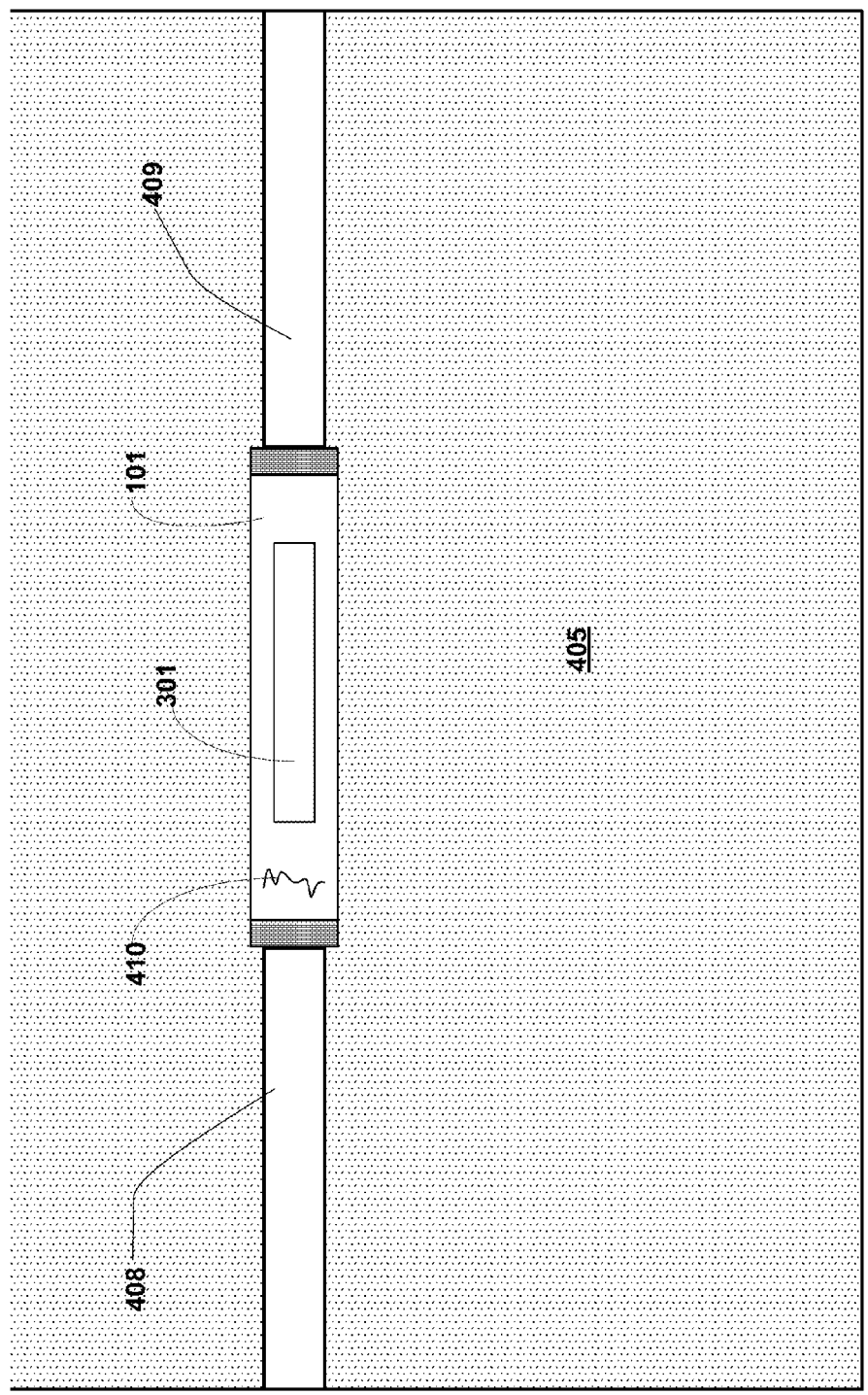
FIG. 4 is a conceptual diagram of the vial with impactor, as used in a cryogenic mill.

FIG. 4 shows in concept the portions of the cryogenic mill. The capped vial 101 is placed in the opening of the coil assembly and supported by means 408, 409, with the sample 410 and impactor 301 installed within the vial. Liquid nitrogen 405 is used to cool the sample 410 down to the point where it can be ground to a powder. The impactor 301 is then caused to rapidly oscillate back and forth, typically by a varying electromagnetic field, generated by one or more coils (see FIG. 5) properly positioned.

Because the steel is surrounded by polycarbonate, any effect the steel would have on degrading or contaminating the sample is avoided, because the surrounding polycarbonate is inert. Moreover, the impact between the polycarbonate surrounding the impactor and the thick polycarbonate end caps is sufficient to cause the grinding of a typical biological or similar sample when cooled to liquid nitrogen temperatures; the purpose of the cryogenic mill is facilitated even without direct contact by the steel.

Figure 5:
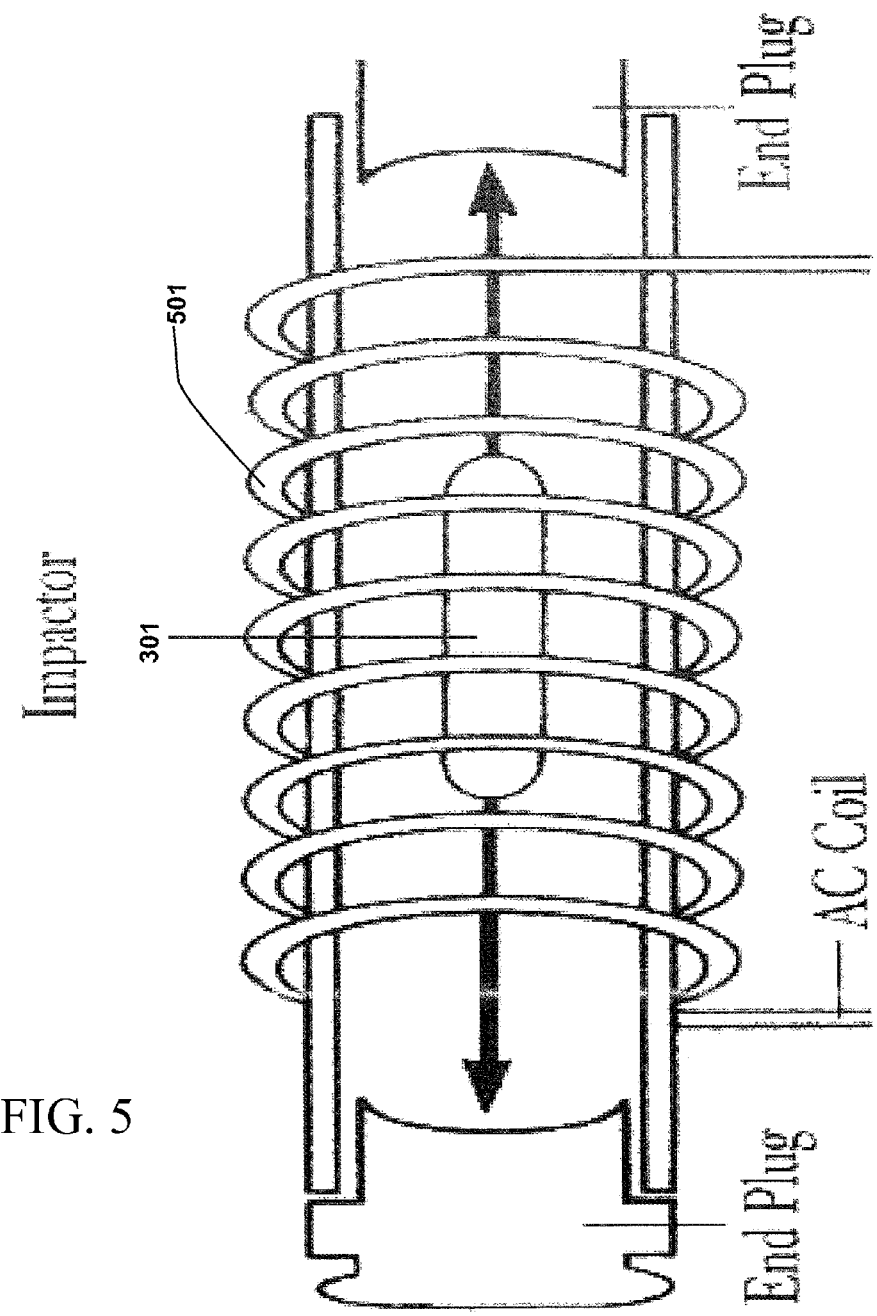
FIG. 5 is an additional diagram of a similar embodiment of the present invention, shown with the coil used to move the impactor.

FIG. 5 shows a view of the vial installed within an electromagnetic coil. By inducing alternating current in the coil 501, the impactor 301 will oscillate but the impact will not include impacting steel directly onto the sample (note shown). Instead, the polycarbonate, inert coating will impact the sample. The frequency and magnitude of the impacts can be adjusted via the frequency and magnitude of the current in the coil 501.

While the foregoing describes the preferred embodiment of the invention, various combinations or additions will be apparent to those of skill in the art. Such combinations are intended to be covered by the following claims.

The invention claimed is:

1. A method for grinding a sample comprising drilling out a first longitudinal member to create a first trough, drilling out a second longitudinal member to create a second trough, placing an impactor core into both first and second troughs, joining said first and second members to substantially enclose said impactor core, and using said enclosed impactor core to repeatedly strike and grind a sample within an enclosure containing the impactor and the sample.

2. The method of claim 1 wherein said first and second longitudinal members are made of polycarbonate.

3. The method of claim 2 wherein said impactor core is made of steel.

4. The method of claim 3 wherein said step of using said enclosed impactor includes placing said enclosed impactor into a vial and subjecting the vial to an electromagnetic field.

5. The method of claim 4 wherein said vial into which said impactor is placed is made at least in part from polycarbonate.

* * * * *

UNITED STATES PATENT AND TRADEMARK OFFICE
Certificate

Patent No. 8,061,633 B2                                    Patented: November 22, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Martin, Annandale, NJ (US); and Donald Van Duyne, Metuchen, NJ (US).

Signed and Sealed this Thirteenth Day of May 2014.

GREGORY L. HUSON
*Supervisory Patent Examiner*
Art Unit 3751
Technology Center 3700